United States Patent [19]

Katsuki et al.

[11] Patent Number: 5,599,957
[45] Date of Patent: Feb. 4, 1997

[54] ASYMMETRIC EPOXIDATION REACTION

[75] Inventors: Tsutomu Katsuki; Ryo Irie; Hidehiko Sasaki, all of Fukuoka, Japan

[73] Assignee: Nissan Chemical Industries, Ltd., Tokyo, Japan

[21] Appl. No.: 452,855

[22] Filed: May 30, 1995

Related U.S. Application Data

[63] Continuation-in-part of Ser. No. 209,723, Mar. 14, 1994, Pat. No. 5,420,314.

[30] Foreign Application Priority Data

Feb. 23, 1994 [JP] Japan ........................... 6-25337

[51] Int. Cl.⁶ .................... C07F 13/00; C07F 9/547; C07D 323/00; C07D 487/00
[52] U.S. Cl. .................... 549/533; 548/126; 548/414; 548/416; 548/417; 549/531; 502/171; 556/35; 556/45
[58] Field of Search ................... 548/126, 414, 548/416, 417; 549/531, 533; 556/45, 33; 502/171

[56] References Cited

U.S. PATENT DOCUMENTS 5,097,037  3/1992  Matsumoto et al. ............... 548/126

FOREIGN PATENT DOCUMENTS

| 0409165 | 1/1991 | European Pat. Off. . |
| 0535377 | 4/1993 | European Pat. Off. . |
| 3-141286 | 6/1991 | Japan . |
| 5-301878 | 11/1993 | Japan . |
| WO91/14694 | 10/1991 | WIPO . |

OTHER PUBLICATIONS

"Synthesis and Antiviral Activity of a Series of HIV–1 Protease Inhibitors with Functionality Tethered to the $P_1$ or $P_1'$ Phenyl Substituents: X-ray Crystal Structure Assisted Design", Wayne J. Thompson et al., *J. Med. Chem.*, 1992, 35, pp. 1685–1701.

"Mechanism of Action and Systemic and Regional Hemodynamics of the Potassium Channel Activator BRL34915 and Its Enantiomers", R. P. Hof et al., *Circulation Research*, vol. 62, No. 4, Apr. 1988, pp. 679–686.

"Highly Enantioselective Epoxidation Catalysts Derived from 1,2–Diaminocyclohexane", Eric N. Jacobsen et al., *J. Am. Chem. Soc.*, 1991, 113, pp. 7063–7064.

"Novel salen complexes having optically active binaphthyl skeleton as a structural element and asymmetric epoxidation reaction which uses said complexes", Hidehiko Sasaki et al., *Nippon Kagakukai (Japan Chemical Society)*, No. 65, Spring–Annual Meeting (published on Mar. 15, 1993).

"Catalytic Asymmetric Epoxidation with (Salen) manganese(III) Complex Bearing Binaphtyhl Groups of Axial Chirality", Hidehiko Sasaki et al., *Synlett*, Letters, pp. 300–302, (1993).

"Organic Synthesis Chemistry Lecture: Architectural Enzyme Salen (Maganese) Complexes and Function Thereof", Ryo Irie, *Organic Synthesis Chemical Society*, Nov. 25 and 26, 1993, pp. 80–89.

"Asymmetric convertion reaction of olefins", Tsutomu Katsuki, *Nippon Kagakukai (Japan Chemical Society)*, No. 66, Autumn –Annual Meeting (published on Sep. 13, 1993), pp. 430.

"Asymmetric Epoxidation Using Chiral Salen Complexes", Ryo Irie, *Bulletin of Organic Synthesis Chemistry Association*, pp. 412–420, (1993).

*Primary Examiner*—Porfirio Nazario-Gonzalez
*Attorney, Agent, or Firm*—Oliff & Berridge

[57] ABSTRACT

An optically active manganese complex of the formula $I_a$, $I_b$, $I_c$ and $I_d$

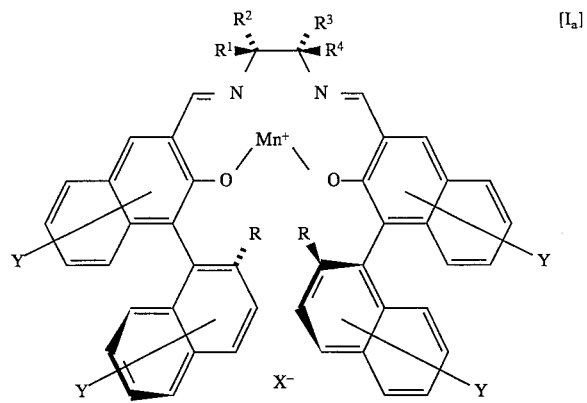

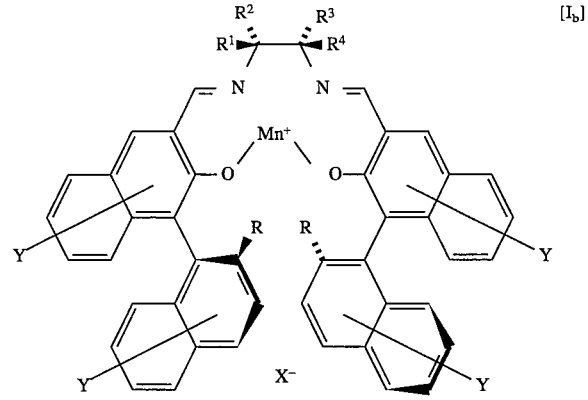

(Abstract continued on next page.)

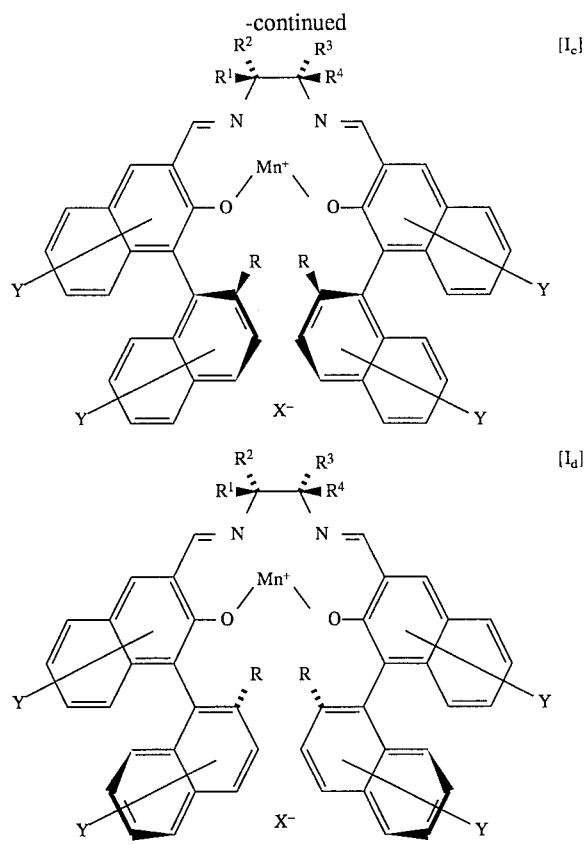

wherein $R^1$, $R^2$, $R^3$ and $R^4$ independently represent hydrogen atom, $C_{1-4}$ alkyl group, phenyl group which may be substituted by a halogen atom, $C_{1-4}$ alkyl group, $C_{1-4}$ alkoxyl group, cyano group or nitro group; and any two of $R^1$, $R^2$, $R^3$ and $R^4$ together form a $C_{4-8}$ ring, $X^-$ represents a counter anion which may form a salt, Y represents hydrogen atom, halogen atom, $C_{1-4}$ alkyl group, $C_{1-4}$ alkoxyl group, nitro group or cyano group, R represents hydrogen atom, $C_{1-4}$ alkyl group, phenyl group which may be substituted by halogen atom, $C_{1-4}$ alkyl group or $C_{1-4}$ alkoxyl group, or substituted silyl group and a process for producing epoxy compounds using the complex as a catalyst.

27 Claims, No Drawings

ASYMMETRIC EPOXIDATION REACTION

This is a continuation-in-part application of application Ser. No. 08/209,723, filed Mar. 14, 1994, now U.S. Pat. No. 5,420,314.

BACKGROUND OF THE INVENTION

1. Field of the Invention

The present invention relates to a process for producing an optically active epoxy compound which is an important intermediate in the synthesis of optically active medicines including benzopyran compounds, etc., for the treatment of hypertension, asthma, etc.

2. Description of the Prior Art

One of the most general methods in case that an epoxy compound is used for preparing optically active medicines is a separation of diastereomer at a further procceded stage (e.g., to treat amino-alcohol compound obtained by reacting the epoxy compound with ammonia). It is exemplified by the optical resolution of pyranobenzoxadiazole compounds described in Japanese Patent Application Laid-Open No. 141286/1991, EP 409165, and U.S. Pat. No. 5,097,037, and also by the synthesis of optically active indene oxide described in J. Med. Chem. 35, 1685–1701 (1992). There is another method which involves the step of making a halohydrin compound (as a precursor of an epoxy compound) into its derivatives and conducting the separation of the diastereomer on it at that step, or which resorts to the stereoselectivity of an enzyme. An example is the optical resolution of benzopyran compounds, which is described in Circulation Research, 62, 4, 679–686 (1988). The foregoing two methods, however, suffer a serious economical disadvantage that as they separate racemic mixture, enantiomer which is not used become completely wasted.

There has recently been found a new process for synthesis which employs an optically active manganese complex as an asymmetric catalyst. This process is attracting attention because of its ability to yield optically active epoxy compounds effectively. Examples of the asymmetric catalyst are given by Jacobsen et al. in J. Am. Chem. Soc., 113, 7063–7064, (1991) and also by Katsuki in Japanese Patent Application Laid-Open No. 301878/1993 and European Patent Laid-Open No. 535377. Unlike the separation of racemic mixture, this process solved the problem that enantiomer which is not used becomes wasted. Therefore, it affords high chemical and optical yields if appropriate olefins are selected as the starting material. However, the catalysts reported so far are not satisfactory for the production of every optically active epoxy compound. Active researches are under way for further improvement.

After the present inventors have conducted their intensive researches, they have found out a process for producing optically active epoxy compounds by using olefin compounds which do not have functional group coordinating with metals such as hydroxy group at the neighbor of a double bond. (Said olefin compounds are hereinafter referred to as "unfunctionalized olefin compound" or "olefin compound having no precoordinating functional group".)

SUMMARY OF THE INVENTION

The present inventors have intensively investigated a process for producing an optically active epoxy compound of the formula III:

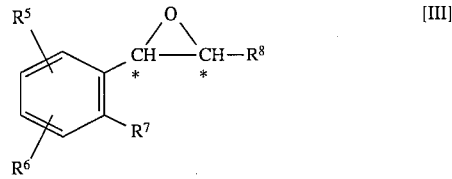

wherein $R^5$ and $R^6$ independently represent a hydrogen atom, cyano group, nitro group, amino group which may be protected by an acetyl group or the like, halogen atom, $C_1$–$C_4$ alkyl group, $C_1$–$C_4$ alkoxyl group, halo-$C_1$–$C_4$ alkyl group, carboxyl group, formyl group, $C_1$–$C_4$ alkanoyl group, aroyl group, halo-$C_1$–$C_4$ alkanoyl group, carbamoyl group, $C_1$–$C_4$ alkylsulfinyl group, arylsulfinyl group, $C_1$–$C_4$ alkylsulfonyl group, arylsulfonyl group, sulfonamide group, or mono- or di-$C_1$–$C_4$ alkylsulfonamide group, or if $R^5$ and $R^6$ are at the ortho position, $R^5$ and $R^6$, together with the linking ring, form a group of the formula:

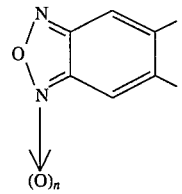

wherein n is 0 or an integer of 1, $R^7$ represents hydrogen atom, $C_1$–$C_4$ alkyl group or $C_1$–$C_4$ alkoxyl group, $R^8$ represents $C_1$–$C_4$ alkyl group or $C_1$–$C_4$ alkoxyl group, $R^7$ and $R^8$ together form the groups of the formulae:

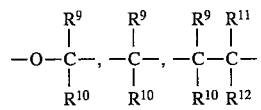

wherein $R^9$, $R^{10}$, $R^{11}$ and $R^{12}$ independently represent a hydrogen atom or $C_1$–$C_4$ alkyl group, and the absolute configuration of the carbon atoms which are marked with asterisks (*) means R or S, from an olefin compound of the formula II:

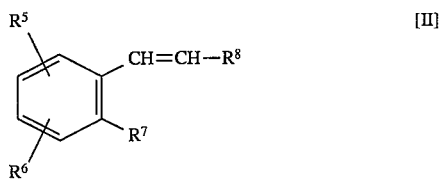

wherein $R^5$, $R^6$, $R^7$ and $R^8$ have the same meanings as defined above, as a starting material. As a result, it has been found that it is possible to produce the intended optically active epoxy compound of the formula III in high asymmetric yields, by using, as an asymmetric catalyst, one or more optically active manganese complex selected from the optically active manganese complexes of the formula $I_a$, $I_b$, $I_c$ and $I_d$:

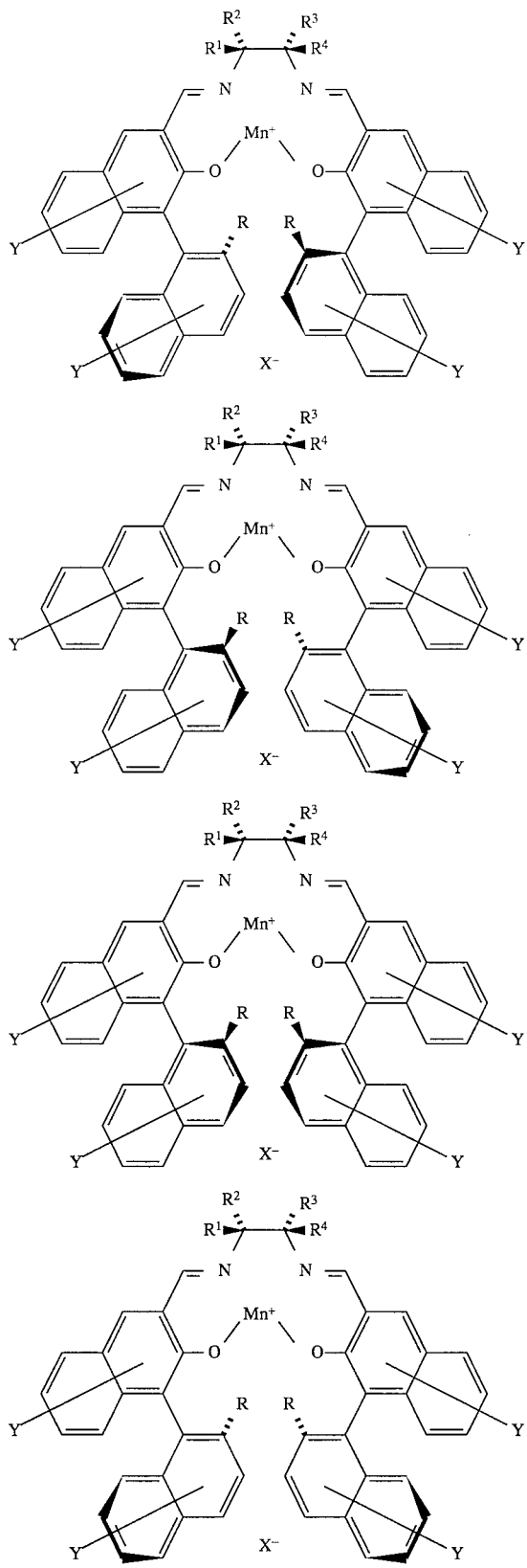

wherein $R^1$, $R^2$, $R^3$, and $R^4$ independently represent hydrogen atom, $C_1$–$C_4$ alkyl group, phenyl group which may be substituted by a halogen atom, $C_1$–$C_4$ alkyl group, $C_1$–$C_4$ alkoxyl group, cyano group or nitro group; and any two of $R^1$, $R^2$, $R^3$ and $R^4$ together form the $C_4$–$C_8$ ring, $X^-$ represents a counter anion which may form a salt, Y represents hydrogen atom, halogen atom, $C_1$–$C_4$ alkyl group, $C_1$–$C_4$ alkoxyl group, nitro group or cyano group, R represents hydrogen atom, $C_1$–$C_4$ alkyl group, phenyl group which may be substituted by halogen atom, $C_1$–$C_4$ alkyl group or $C_1$–$C_4$ alkoxyl group, or substituted silyl group. The present invention has been completed on the basis of this finding.

DESCRIPTION OF THE PREFERRED EMBODIMENTS

The optically active manganese complexes $[I_a]$, $[I_b]$, $[I_c]$ and $[I_d]$ have substituent groups $R^1$, $R^2$, $R^3$ and $R^4$, each of which may be hydrogen atom, $C_1$–$C_4$ alkyl group or phenyl group. The $C_1$–$C_4$ alkyl group may be any one of methyl group, ethyl group, normal-propyl group, isopropyl group, normal-butyl group, isobutyl group, secondary butyl group and tertiary butyl group. The phenyl group may be substituted by any of fluorine atom, chlorine atom, bromine atom, methyl group, ethyl group, normal-propyl group, isopropyl group, normal-butyl group, isobutyl group, secondary butyl group, tertiary butyl group, methoxy group, ethoxy group, normal-propoxy group, isopropoxy group, normal-butoxy group, isobutoxy group, secondary butoxy group, tertiary butoxy group, cyano group and nitro group. Of these substituent groups, any of hydrogen atom, ethyl group, tertiary butyl group, phenyl group and 3,5-dimethylphenyl group are preferable.

Any two of the substituents $R^1$, $R^2$, $R^3$ and $R^4$ may together form a $C_4$–$C_8$ ring such as cyclobutane, cyclopentane, cyclohexane, cycloheptane and cyclooctane.

The group R includes a phenyl group, fluorophenyl group, chlorophenyl group, bromophenyl group, tolyl group, ethylphenyl group, tertiary butylphenyl group, 3,5-dimethylphenyl group, methoxyphenyl group (of ortho, meta and para isomers), hydrogen atom, methyl group, ethyl group, isopropyl group, normal-propyl group, normal-butyl group, isobutyl group, secondary butyl group, tertiary butyl group and substituted silyl group.

Examples of the substituted-silyl group include trimethylsilyl, triethylsilyl, tri-normal-propylsilyl, triisopropylsilyl, tri-normal-butylsilyl, triisobutylsilyl, tri-normal-hexylsilyl, dimethylethylsilyl, dimethyl-normal-propylsilyl, dimethyl-normal-butylsilyl, dimethylisobutylsilyl, dimethyl-tertiary-butylsilyl, dimethyl-normal-pentylsilyl, dimethyl-normal-octylsilyl, dimethylcyclohexylsilyl, dimethylthexylsilyl, dimethyl-2,3-dimethylpropylsilyl, dimethyl-2-(bicycloheptyl)silyl, dimethylbenzylsilyl, dimethylphenylsilyl, dimethyl-para-tolylsilyl, dimethylflophemesylsilyl, methyldiphenylsilyl, triphenylsilyl, diphenyl-tertiary-butylsilyl, tribenzylsilyl, diphenylvinylsilyl, diphenyl-normal-butylsilyl and phenylmethylvinylsilyl.

Examples of Y include a hydrogen atom, halogen atom such as fluorine atom, chlorine atom and bromine atom, methyl group, ethyl group, normal-propyl group, isopropyl group, normal-butyl group, isobutyl group, secondary butyl group, tertiary butyl group, methoxy group, ethoxy group, normal propoxy group, isopropoxy group, normal-butoxy group, isobutoxy group, secondary butoxy group, tertiary butoxy group, nitro group and cyano group.

The optically active manganese complex [$I_a$], [$I_b$], [$I_c$] and [$I_d$] can form a salt together with various kinds of the counter anion ($X^-$) as a manganese which is a metal center can be monovalent to pentavalent oxidized state. The examples of the counter anion include monovalent $OH^-$, $F^-$, $Cl^-$, $Br^-$, $I^-$, $CH_3CO^-$, $PF_6^-$, $ClO_4^-$ and $BF_4^-$ ions; divalent $CO_3^{2-}$ and $SO_4^{2-}$ ions; and trivalent $PO_4^{3-}$ ion. All of these salts can be used as asymmetric catalyst of the present invention.

The following is the typical synthesis examples of the optically active manganese complex [$I_a$], [$I_b$], [$I_c$] and [$I_d$].

Scheme 1 shows a synthesis method of only the compound of the formula [$I_a$] wherein $R^1=R^3=R=Ph$ (phenyl group), $R^2=R^4=H$ and $X=CH_3CO_2^-$. Since the compound [$I_a$] and the compound [$I_b$] are in the relation of antipode to each other, it is enough to simply replace the optically active binaphthol and diamine as the starting materials with ones having the opposite configuration in order to synthesize the compound [$I_b$] wherein $R^1=R^3=Ph$ (phenyl group), $R^2=R^4=H$, and $X=CH_3CO_2^-$.

The optically active manganese complexes [$I_c$] and [$I_d$] may be obtained as a mixture containing the optically active manganese complexes [$I_a$] and [$I_b$] by synthesizing a salicylaldehyde compound with the use of an optically active binaphthol compound as a starting material which has lower optical purity or is a racemic mixture, reacting the synthesized compound with diamine compound to form an imine compound, and synthesizing a manganese complex from the imine compound.

Moreover, the optically active manganese complexes [$I_c$] and [$I_d$] may be synthesized by purifying an imine compound and synthesizing the manganese complex.

According to Scheme 1, the synthesis consists of the steps of (a) reacting an optically active binaphthol having the molecular asymmetry with N-phenyltrifluoromethane-sulfonimide in the presence of collidine, thereby converting one of the hydroxy groups as a triflate; (b) substituting the triflate with a phenyl Grignard reagent, using chloro[1,2bis(diphenylphosphino)ethane]nickel (II) as a catalyst; (c) conducting methoxymethylation with chloromethyl methyl ether under basic conditions; (d) conducting lithiation with tertiary-butyl lithium; (e) conducting formylation with dimethylformamide; and (f) conducting demethoxylmethylation with trimethylsilyl bromide, thereby yielding a salicyl aldehyde compound. The synthesis of a compound in which R group is different can be prepared by changing the kind of Grignard reagents in the step (b). As the diamine compounds which are the other starting material, marketed ones are used.

Scheme 2 shows a case of the synthesis of a noncommercial diamine wherein $R^1=R^3=3,5$-dimethylphenyl group and $R^2=R^4=H$. Namely, Scheme 2, the synthesis consists of the steps of (g) converting 3,5-dimethylbenzoic acid into alcohol by reduction with lithium aluminum hydride; (h) converting it into aldehyde by oxidation with manganese dioxide; (i) performing dimerization by the aid of titanium tetrachloride and zinc dust; (j) converting the dimer into a high-purity optically active diol by Sharpless asymmetric dihydroxylation reaction, using osmium tetraoxide having hydroquinidine 4-chlorobenzoate as the asymmetric source; (k) mesylating the hydroxyl group with mesyl chloride under basic conditions; (l) performing the substitution reaction with sodium azide; and (m) reducing the azide with lithium aluminum hydride, thereby yielding the intended diamine compound. The foregoing procedure is not limitative because there are several ways of synthesis according to the kinds of the substituents.

The salicyl aldehyde compound and the diamine compound obtained as described above are mixed in a solvent to give an imine compound. Examples of the solvent include alcohols such as ethanol and methanol, nitriles such as acetonitrile and propionitrile, halogenated hydrocarbons such as dichloromethane and chloroform, aromatic hydrocarbons such as benzene and toluene, ethers such as tetrahydrofuran and diethyl ether, and aliphatic hydrocarbons such as hexane and heptane. Of these solvents, ethanol, methanol, acetonitrile, dichloromethane, and toluene are preferable. If necessary, the solvent may be used in combination with more than equimolar amount of dehydrating agent, such as anhydrous magnesium sulfate, boric anhydride, and Molecular Sieves. Alternatively, the solvent may be dehydrated by azeotropic dehydration. The reaction temperature is not specifically limited, but it ranges from $-20°$ C. to the boiling point of the solvent used, preferably, from $0°$ C. to $50°$ C. It is not always necessary to separate the imine from the reaction mixture; it may remain in the reaction mixture as a following procedure in the synthesis of the manganese complex.

The thus obtained imine compound is dissolved or suspended in an alcohol solvent such as ethanol and methanol, a nitrile solvent such as acetonitrile and propionitrile, and a halogenated hydrocarbon solvent such as dichloromethane and chloroform. Manganese acetate in an amount of 0.5–10 molar equivalent, preferably 0.8–2 molar equivalent, is added to the solution or suspension. Reaction is carried out in the presence of oxygen to give the intended optically active manganese complex [$I_a$], [$I_b$], [$I_c$] or [$I_d$]. If necessary, the $CH_3CO_2^-$ ion may be replaced by $Cl^-$, $PF_6^-$, or any other anion. Replacement by the $Cl^-$ ion may be accomplished by adding more than equimolar amount of lithium chloride to the reaction mixture. Examples of the preferred solvent include ethanol, methanol, acetonitrile and dichloromethane. The reaction temperature is not specifically limited; it may range from $-20°$ C. to the boiling point of the solvent used. The preferred reaction temperature ranges from $0°$ C. to $50°$ C. Oxygen required for the reaction may be supplied by blowing a large excess of air or oxygen gas into the reaction mixture or by stirring, with the reaction system open to the atmosphere.

Scheme 3 shows the synthesis of the optically active manganese complex [$I_a$] wherein $R^1=R^3=Ph$ (phenyl group), $R^2=R^4=H$, and $X=CH_3CO_2$ in which a diamine compound is (1S, 2S)-1,2-diphenyl-1,2-ethanediamine.

Preferably, a mixture of the optically active manganese complexes $I_a$, $I_b$, $I_c$ and $I_d$ is used as an asymmetric catalyst in an epoxidation reaction, most preferably in a ratio of about 1:1:1:1.

Scheme 1

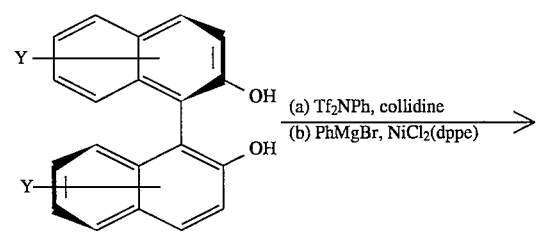

Scheme 1 -continued

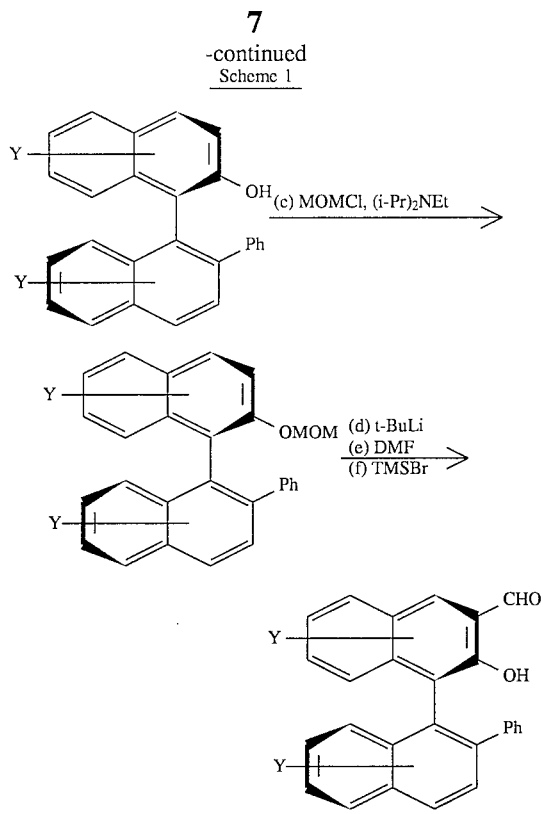

Scheme 2

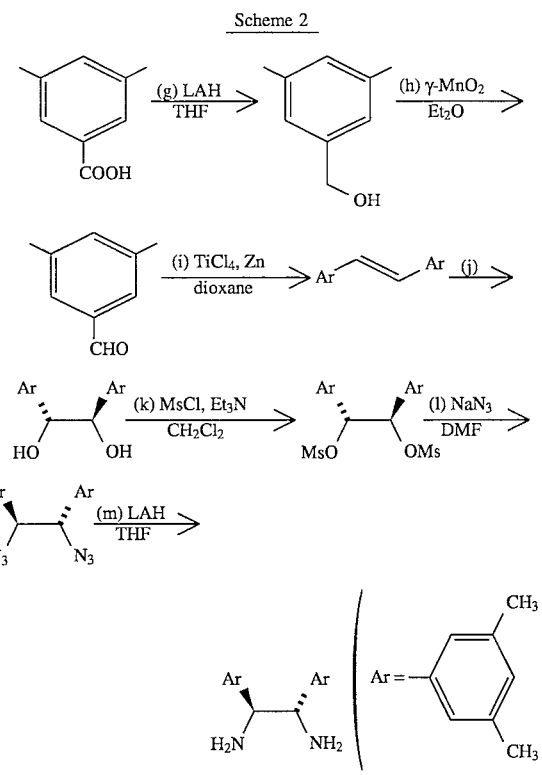

Scheme 3

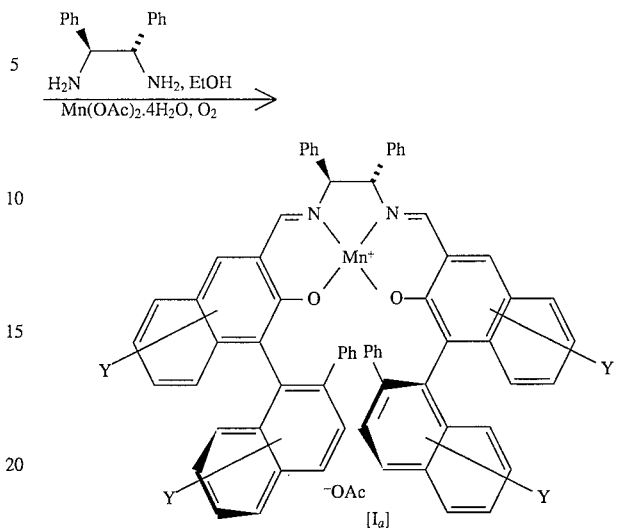

wherein Ph represents phenyl, Tf$_2$NPh represents N-phenyltrifluoromethanesulfonimide, PhMgBr represents phenyl magnesium bromide, NiCl$_2$(dppe) represents chloro[1,2-bis(diphenylphosphino)ethane]nickel (II), MOMCl represents chloromethyl methyl ether, (i-Pr)$_2$NEt represents diisopropylethylamine, THF represents tetrahydrofuran, DMF represents dimethylformamide, TMSBr represents trimethylsilyl bromide, LAH represents lithium aluminum hydride and Et$_2$O represents diethyl ether.

The following description is about the concrete process for asymmetric epoxidation.

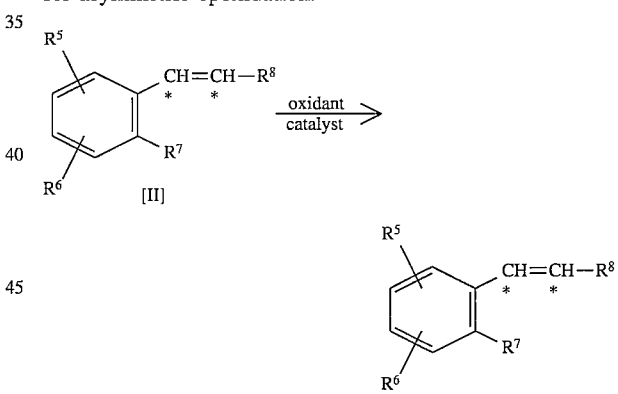

Asymmetric catalyst, namely, the amount of the optically active manganese complex [I$_a$], [I$_b$], [I$_c$] or [I$_d$] or the total amount of the optically active manganese complexes [I$_a$], [I$_b$], [I$_c$] and [I$_d$] is used in the range of, namely, from 0.1 mol % to 100 mol %, preferably from 1 mol % to 5 mol %, based on the mole of the olefin compound [II] as the starting material. Examples of usable oxidizing agents include iodosylbenzene, 2-iodosylbenzoic acid, sodium hypochlorite, tetrabutylammonium periodate, hydrogen peroxide, oxygen, and air. When iodosylbenzene or 2-iodosylbenzoic acid is used as the oxidizing agent, it is normally used in the range of from 1 equivalent to 10 equivalents, preferably 1 equivalent to 3 equivalents, based on the olefin compound [II]. When sodium hypochlorite, tetrabutylammonium periodate, or hydrogen peroxide is used as the oxidizing agent, it is normally used in the range of 1 equivalent to 100 equivalents, preferably 3 equivalents to 30 equivalents, based on the olefin compound [II]. Oxidation with a large excess of air or oxygen gas may be accomplished by blowing air in large excess or oxygen in large excess into the reaction mixture or by stirring, with the reaction mixture open to the atmosphere.

As a medium for the reaction, there can be used water, acetonitrile, dichloromethane, dichloroethane and a mixture thereof. Especially, when sodium hypochlorite is used as the oxidizing agent, it may be preferable to use a two-phase system such as water and dichloromethane. Also, there can co-exist a component having coordination ability with the manganese complex such as pyridine N-oxide, 4-phenylpyridine N-oxide, lutidine N-oxide or 2-methylimidazole. There is no particular limitation on the quantity of the components to be used.

The reaction is ordinarily carried out at a temperature in the range of from −50° C. to 50° C., preferably from −20° C. to 25° C.

After the completion of the reaction, the organic solvent is distilled off under reduced pressure to concentrate the reaction solution and only separated and purified by using a silica gel column chromatography or distillation to isolate the intended optically active compound [III]. The optical purity of the optically compound [III] can be analyzed by optically active liquid chromatography (using, e.g., Chiralcel OJ mfd. by Daicel Chemical Industries, Ltd.) or optical rotation, under conditions as shown in Examples.

Examples of the olefin compound [II] to which the asymmetric epoxidation reaction of the present invention may be applied include a benzopyran derivative of formula IV:

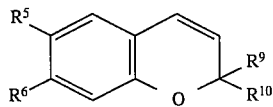 [IV]

wherein $R^5$ and $R^6$ independently represent hydrogen atom, cyano group, nitro group, amino group which may be protected by an acetyl group or the like, halogen atom, $C_1$–$C_4$ alkyl group, $C_1$–$C_4$ alkoxyl group, halo-$C_1$–$C_4$ alkyl group, carboxyl group, formyl group, $C_1$–$C_4$ alkanoyl group, aroyl group, halo-$C_1$–$C_4$ alkanoyl group, carbamoyl group, $C_1$–$C_4$ alkylsulfinyl group, arylsulfinyl group, $C_1$–$C_4$ alkylsulfonyl group, arylsulfonyl group, sulfonamide group, or mono- or di-$C_1$–$C_4$ alkylsulfonamide group, $R^5$ and $R^6$ may together form a ring represented by the following formula:

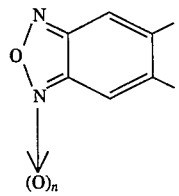

wherein n is 0 or an integer of 1, $R^9$ and $R^{10}$ independently represent hydrogen atom or $C_1$–$C_4$ alkyl group, or an indene derivative of the formula VI:

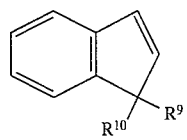 [VI]

wherein $R^9$ and $R^{10}$ have the same meanings defined above.

Preferred benzopyran derivatives may be represented by the formula:

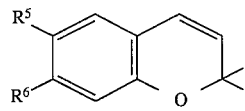

wherein $R^5$ and $R^6$ independently represent hydrogen atom, cyano group, nitro group, amino group which may be protected by acetyl group or the like, halogen atom, $C_1$–$C_4$ alkyl group, $C_1$–$C_4$ alkoxyl group, halo-$C_1$–$C_4$ alkyl group, carboxyl group, formyl group, $C_1$–$C_4$ alkanoyl group, aroyl group, halo-$C_1$–$C_4$ alkanoyl group, carbamoyl group, $C_1$–$C_4$ alkylsulfinyl group, arylsulfinyl group, $C_1$–$C_4$ alkylsulfonyl group, arylsulfonyl group, sulfonamide group or mono- or di-$C_1$–$C_4$ alkylsulfonamide group, and a compound of the formula:

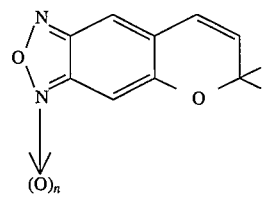

wherein n is 0 or an integer of 1.

Preferred indene derivative may be represented by the formula:

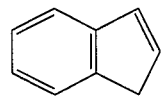

Any of these derivatives yields the intended epoxy compound when processed as described above.

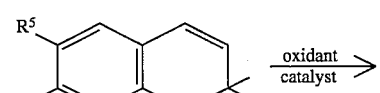

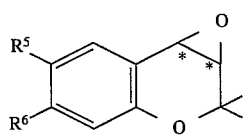

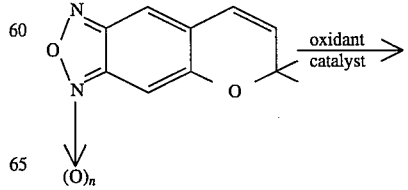

11
-continued

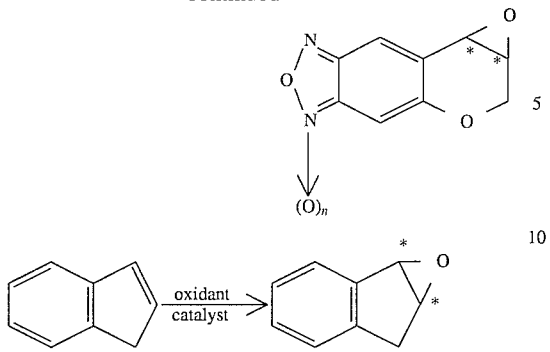

R⁵ and R⁶ which are the substituents of the compounds of the formulae IV and V independently represent hydrogen atom, cyano group, nitro group, amino group which may be protected by acetyl group or the like, halogen atom, $C_1$–$C_4$ alkyl group, $C_1$–$C_4$ alkoxyl group, halo-$C_1$–$C_4$ alkyl group, carboxyl group, formyl group, $C_1$–$C_4$ alkanoyl group, aroyl group, halo-$C_1$–$C_4$ alkanoyl group, carbamoyl group, $C_1$–$C_4$ alkylsulfinyl group, arylsulfinyl group, $C_1$–$C_4$ alkylsulfonyl group, arylsulfonyl group, sulfonamide group, or mono- or di-$C_1$–$C_4$ alkylsulfonamide group, or R⁵ and R⁶, together with the linking ring, form the formula:

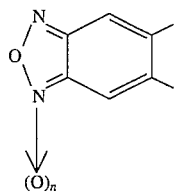

wherein n is 0 or an integer of 1.

Examples of the protecting group of the amino group include acyl groups such as acetyl group, propionyl group, trifluoroacetyl group, and benzoyl group, alkoxycarbonyl group such as methoxycarbonyl group, ethoxycarbonyl group, tertiary butoxycarbonyl group, tosyl group, and benzyl group, preferably, acetyl group and tertiary butoxycarbonyl group.

The halogen atom includes fluorine atom, chlorine atom, bromine atom and iodine atom.

The $C_1$–$C_4$ alkyl group includes methyl group, ethyl group, normal-propyl group, isopropyl group, normal-butyl group, isobutyl group, secondary butyl group and tertiary butyl group.

The $C_1$–$C_4$ alkoxyl group includes methoxy group, ethoxy group, normal-propoxy group, isopropoxy group, normal-butoxy group, isobutoxy group, secondary butoxy group and tertiary butoxy group.

The halo-$C_1$–$C_4$ alkyl group represents any group formed by substituting the above-described $C_1$–$C_4$ alkyl group with a halogen atom. It includes trifluoromethyl group, monochloromethyl group, pentafluoroethyl group, etc.

The $C_1$–$C_4$ alkanoyl group includes acetyl group and propionyl group.

The aroyl group includes benzoyl group, toluoyl group and naphthoyl group.

The halo-$C_1$–$C_4$ alkanoyl group includes trifluoroacetyl group, monochloroacetyl group and pentafluoropropionyl group.

The $C_1$–$C_4$ alkyl group in the $C_1$–$C_4$ alkylsulfinyl group, $C_1$–$C_4$ alkylsulfonyl group, and mono- and di-$C_1$–$C_4$ alkylsulfonamide is defined as described above. The aryl group in

12 the arylsulfinyl group and arylsulfonyl group includes a phenyl group and tolyl group.

The present invention described above provides a new catalyst to be used to produce, from an olefin compound having no precoordinating functional group, an optically active epoxy compound useful as an optically active medicine or an intermediate compound thereof.

The present invention will further be illustrated by examples.

EXAMPLES

Referential Example 1

Five compounds (1 to 5) represented by the formulae below were prepared.

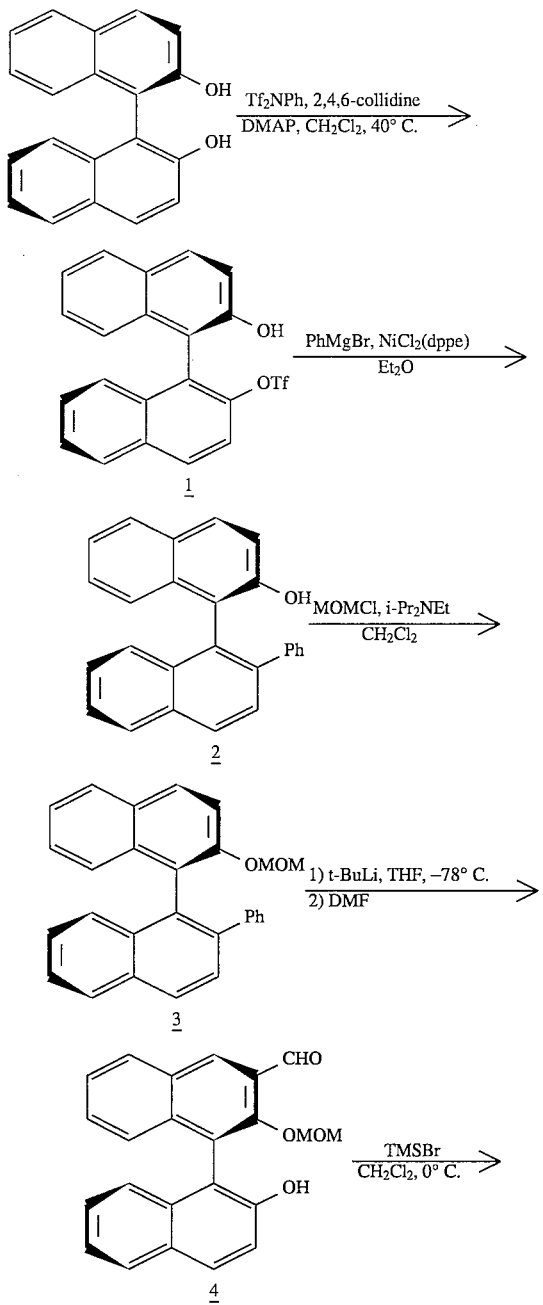

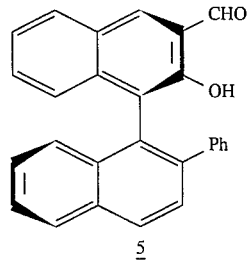

wherein Ph represents phenyl, Tf$_2$NPh represents N-phenyl-trifluoromethanesulfonimide, PhMgBr represents phenyl magnesium bromide, NiCl$_2$(dppe) represents chloro[1,2-bis(diphenylphosphino)ethane]nickel (II), MOMCl represents chloromethyl methyl ether, (i-Pr)$_2$NEt represent diisopropylethylamine, THF represents tetrahydrofuran, DMF represents dimethylformamide, TMSBr represents trimethylsilyl bromide, DMAP represents dimethylaminopyridine, and Et$_2$O represents diethyl ether.

Synthesis of the compound 1

To 4 mL of dichloromethane solution of 286 mg of (R)-(+)-binaphthol (1.0 mmol) were successively added 132 µL of 2,4,6-collidine (1.0 mmol), 15 mg of dimethylaminopyridine (0.12 mmol), and 357 mg of N-phenyltrifluoromethanesulfonimide (1.0 mmol). After refluxing for twelve hours, the reaction mixture was concentrated and the residues were purified by silica gel column chromatography (eluent: toluene) to obtain the intended compound as colorless crystals, (yield: 378 mg (90%)).

Synthesis of the compound 2

To a mixture of 209 mg of the compound 1 (0.5 mmol) and 5.3 mg of chloro [1,2-bis(diphenylphosphino)ethane] nickel (II) (0.01 mmol) was slowly added 2.5 mL of phenyl magnesium bromide (in the form of diethyl ether solution containing 0.8M, 2.0 mmol). After refluxing for one hour, the reactants were cooled to room temperature and the reaction product was suspended by the addition of a saturated aqueous ammonium chloride solution. The reaction mixture was extracted with diethyl ether, and the organic layer was washed successively with a saturated aqueous sodium hydrogen carbonate solution and a saturated aqueous sodium chloride solution. The extract was dried over anhydrous magnesium sulfate and then concentrated. The residues were purified by silica gel column chromatography (eluent: hexane-toluene-4:6) to obtain the intended compound as colorless crystals (yield: 156 mg (90%)).

$^1$H NMR (400 MHz): 8.10 (d, J=8.30Hz, 1H), 7.79 (d, J=8.30 Hz, 1H), 7.78 (d, J=9.28 Hz, 2H), 7.72 (d, J=8.79 Hz, 1H), 7.54–7.50 (m, 1H), 7.36–7.20 (m, 4H), 7.15–7.04 (m, 7H)

Synthesis of the compound 3

To 4 mL of a dichloromethane solution of 365 mg of the compound 2 (1.1 mmol) were successively added 530 BL of diisopropylethylamine (3.0 mmol) and 230 BL of chloromethyl methyl ether (3.0 mmol). After stirring at room temperature for one day, the reaction mixture was washed with water, dried over anhydrous sodium sulfate, and then concentrated. The residues were purified by silica gel column chromatography (eluent: hexane-diethyl ether=19:1) to obtain the intended compound as colorless crystals (yield: 346 mg (83%).

1H NMR (90 MHz): 7.00–8.22 (m, 18H), 4.90 (ABq, J=7.07 Hz, 2H), 2.11 (s, 3H)

Synthesis of the compound 4

140 mg of the compound 3 (0.36 mmol) was dissolved in 1.5 mL of tetrahydrofuran, and the solution was cooled to −78° C. To the solution was added 530 µL of tertiary butyl lithium (in the form of pentane solution containing 1.5M, 0.8 mmol). After stirring at −78° C. for three hours, 140 µL of dimethylformamide (1.8 mmol) was added. Stirring was continued for one hour, with the cooling bath removed. A saturated aqueous ammonium chloride solution was added to stop the reaction. The reaction mixture was extracted with diethyl ether. The organic layer was washed successively with a saturated aqueous sodium hydrogen carbonate solution and a saturated aqueous sodium chloride solution. The extract was dried over anhydrous sodium sulfate and then concentrated. The residues were purified by silica gel column chromatography (eluent: hexane-diethyl ether=19:1) to obtain the intended compound as yellowish crystals (yield: 139 mg (91%)).

1H NMR (90 MHz): 10.42 (s, 1H), 8.50–7.00 (m, 17H), 4.53 (ABq, J=6.17 Hz, 2H), 2.94 (s, 3H)

Synthesis of compound 5

1.5 mL of dichloromethane was added to a mixture of 154 mg of the compound 4 (0.37 mmol) and Molecular Sieve 4A. With the reactants cooled to 0° C., 195 µL of trimethylsilyl bromide (1.5 mmol) was added, followed by stirring for four hours. A saturated aqueous sodium hydrogen carbonate solution was added to stop the reaction. The reaction mixture was extracted with dichloromethane. The organic layer was dried over anhydrous magnesium sulfate and then concentrated. The residues were purified by silica gel column chromatography (eluent:hexane-toluene=3:7) to obtain the intended compound as yellowish crystals (yield: 132 mg (95%)).

$^1$H NMR (400 MHz): 10.41 (s, 1H), 10.10 (s, 1H), 8.17 (s, 1H) 8.05 (d, J=8.30 Hz, 1H), 7.97 (d, J=8.30 Hz, 1H), 7.85 (d, J=7.81 Hz, 1H), 7.49 (t, J=3.42 Hz, 1H), 7.34–7.19 (m, 6H), 7.02–7.00 (m, 3H)

Referential Example 2

Six compounds (6 to 12) represented by the formulae below were prepared.

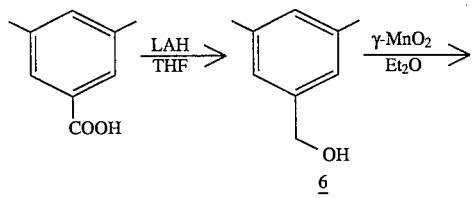

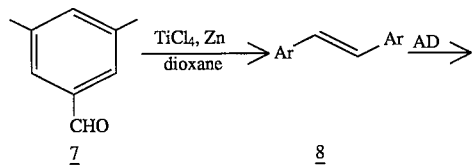

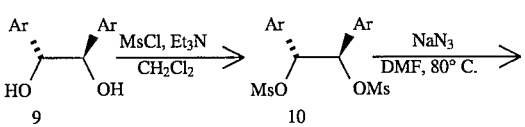

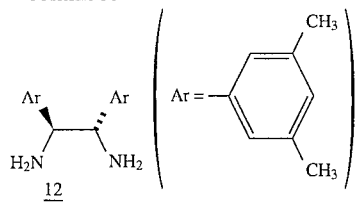

wherein LAH represents lithium aluminum hydride, THF represents tetrahydrofuran, Et$_2$O represents diethyl ether, MsCl represents mesyl chloride and DMF represents dimethyl formamide.

Synthesis of compound 6

To 120 mL of a tetrahydrofuran solution of 4.5 g of 3,5-dimethylbenzoic acid (30 mmol) was slowly added 7.7 g of lithium aluminum hydride (45 mmol), with the temperature kept at 0.° C. After refluxing for two hours, 8 mL of methanol and 50 mL of 3N hydrochloric acid were added to stop the reaction. The reaction mixture was extracted with diethyl ether. The organic layer was washed successively with a saturated aqueous sodium hydrogen carbonate solution and a saturated aqueous sodium chloride solution. The extract was dried over anhydrous magnesium sulfate and then concentrated. The residues were purified by silica gel column chromatography (eluent: hexane-ethyl acetate=8:2) to obtain the intended compound as colorless oil (yield: 3.0 g (74%)).

Synthesis of compound 7

To 8.60 g of a diethyl ether solution of the compound 6 (63 mmol) was added 54.8 g of gamma-manganese oxide (630 mmol), followed by stirring at room temperature for sixteen hours. The reaction mixture was filtered through Celite. 8.05 g of the resulting crude product was used as such for the subsequent reaction.

Synthesis of compound 8

8.05 g of the crude product (the compound 7) (60 mmol) was dissolved in 400 mL of dioxane. To the solution were added 9.9 mL of titanium tetrachloride (90 mmol) and 11.8 g of zinc dust (180 mmol), both suspended in 200 mL of dioxane. After refluxing for four hours, the reaction mixture was partitioned into water and diethyl ether. The organic layer was separated and dried over anhydrous magnesium sulfate and then concentrated. The residues were recrystallized from ethanol to obtain the intended compound as colorless crystals (yield: 3.45 g (48% based on the compound 6)).

$^1$ NMR (90 MHz): 7.24 (s, 4H), 7.14 (s, 2H), 7.00 (s, 2H), 2.36 (s, 12H)

Synthesis of compound 9

A mixture was prepared from 186 mg of hydroquinidine 4-chlorobenzoate (0.4 mmol), 2.96 g of potassium ferricyanide (9.0 mmol), and 1.24 g of potassium carbonate (9.0 mmol). To the mixture were successively added 20 mL of tertiary butanol, 20 mL of water, 11.1 mg of potassium osmate (VI) dihydrate (0.03 mmol), and 709 mg of the compound 8 (3.0 mmol), followed by stirring at room temperature for twenty four hours. 15 g of sodium sulfite (0.12 mmol) was added to the resultant mixture, and stirring was continued for thirty minutes. After separation into two layers, the aqueous layer was extracted with dichloromethane and the extract was combined with the organic layer. After concentration, the residues were diluted with ethyl acetate and the solution was washed successively with 1M sulfuric acid, a saturated aqueous sodium hydrogen carbonate solution, and a saturated aqueous sodium chloride solution. The solution was dried over anhydrous sodium sulfate and then concentrated. The residues were purified by silica gel column chromatography (eluent: hexane-ethyl acetate=9:1–7:3) to obtain the intended compound as colorless crystals (yield: 550 mg (67%)).

The compound 9 was found to have an optical purity higher than 99% e.e., which was determined by the high-performance liquid chromatography that employs a chiral column (Daicel Chiralcel OD and eluent of hexane-isopropanol =15:1).

$^1$H NMR (90 MHz): 6.96 (m, 6H), 4.76 (s, 2H), 2.63 (br, s, 2H), 2.30 (s, 12H)

Synthesis of compound 10

To 8 mL of a dichloromethane solution of 550 mg of the compound 9 (2.0 mmol) were sequentially added 610 µL of triethylamine (4.4 mmol) and 340 µL of mesyl chloride (4.4 mmol), followed by stirring at room temperature for three hours. The reaction mixture was washed with water and then concentrated. The residues were purified by silica gel column chromatography (eluent: diethyl ether) obtain the intended compound as colorless crystals (yield: 839 mg (98%)).

$^1$H NMR (90 MHz): 6.80–7.10 (m, 6H), 5.74 (s, 2H), 2.86 (s, 6H), 2.23 (s, 12H)

Synthesis of compound 11

16 mL of dimethylformamide was added to a mixture of 1.7 g of the compound 10 (4.0 mmol) and 572 mg of sodium azide (8.8 mmol), followed by stirring at 80° C. for seven hours. The reaction mixture was partitioned into water and ethyl acetate, and the organic layer was separated and dried over anhydrous sodium sulfate and then concentrated. The residues were purified by silica gel column chromatography (eluent: hexane) to obtain the intended compound as colorless crystals (yield: 568 mg (48%)).

$^1$H NMR (90 MHz): 7.00 (br, s, 2H), 6.84 (br, s, 2H), 4.63 (s, 2H), 2.28 (s, 12H)

Example 1 Synthesis of the compound [I$_a$-1] of the present invention (Compound 12)

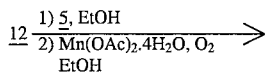

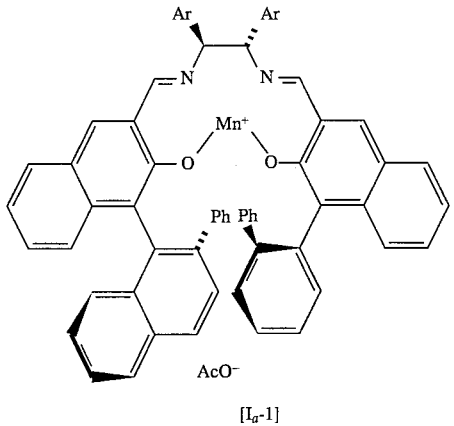

wherein EtOH represents ethanol.

32 mg of the compound 11 (0.1 mmol) was dissolved in tetrahydrofuran. 7.6 mg of lithium aluminum hydride (0.2 mmol) was added to the tetrahydrofuran solution (1 mL) cooled ho 0° C. The mixture was stirred at room temperature for thirty minutes, and 380 µL of a saturated aqueous potassium fluoride solution (1.59 N, 0.6 mmol) was added to stop the reaction. The reaction mixture was filtered through Celite and extracted with ethyl acetate. The extract was dried over anhydrous sodium sulfate and then concentrated. The resulting crude product of the compound 12 and 75.8 mg of the compound 5 (0.2 mmol) were dissolved in 4 mL of ethanol, followed by stirring at room temperature for one hour. The reaction mixture was concentrated and added with 24.6 mg of manganese acetate tetrahydrate (0.1 mmol) and 4 mL of ethanol, followed by stirring in the air for six hours. The resulting crystals were filtered off and washed successively with ethanol and then with hexane to obtain 39.3 mg of the compound [$I_a$-1]. The filtrate was concentrated and the residues were recrystallized from dichloromethane-hexane to obtain 7.7 mg of the compound [$I_a$-1]. (total yield: 47.0 mg (43% based on the compound 11)).

IR (KBr): 3053, 2920, 1599, 1493, 1425, 1333, 1296, 1223, 1188, 1148, 1128, 1045, 1028, 953, 860, 733, 700, 575, 548 cm$^{-1}$

The same procedure as described above was repeated to obtain the compound [$I_a$-2] to [$I_a$-8] of the present invention.

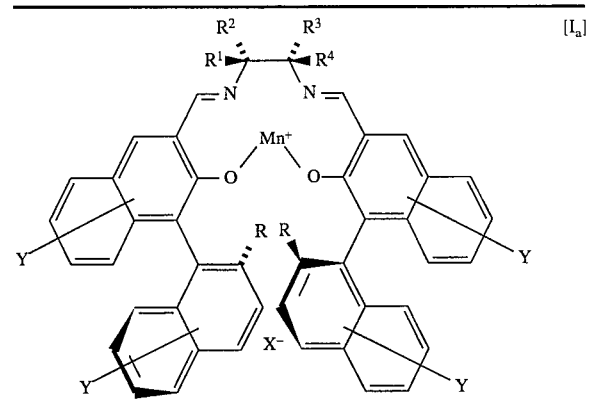

[$I_a$]

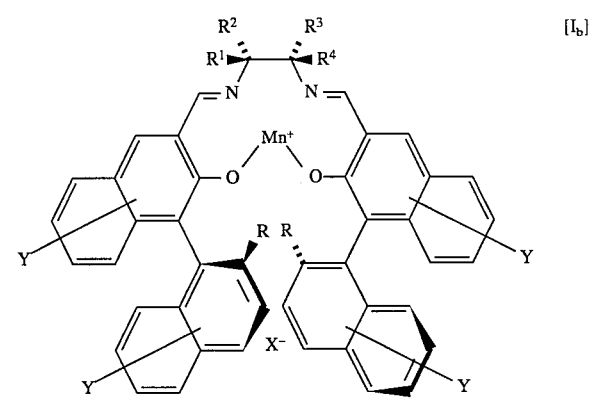

[$I_b$]

| No. | R$^1$ | R$^2$ | R$^3$ | R$^4$ | R | X$^-$ | Y |
|---|---|---|---|---|---|---|---|
| $I_a$-1 | Ar | H | Ar | H | Ph | AcO$^-$ | H |
| $I_a$-2 | Ar | H | Ar | H | Ar | AcO$^-$ | H |
| $I_a$-3 | Ph | H | Ph | H | Ph | AcO$^-$ | H |
| $I_a$-4 | Ph | H | Ph | H | H | AcO$^-$ | H |
| $I_a$-5 | Ph | H | Ph | H | Me | AcO$^-$ | H |
| $I_a$-6 | H | Ph | H | Ph | Me | AcO$^-$ | H |
| $I_a$-7 | a) | H | a) | H | Ph | AcO$^-$ | H |
| $I_a$-8 | a) | H | a) | H | Me | AcO$^-$ | H |
| $I_b$-1 | Ph | H | Ph | H | Ph | AcO$^-$ | H |

Ar = 3,5-dimethylphenyl, Ph = phenyl, Aco$^-$ = CH$_3$CO$_2^-$ a) R$^1$ and R$^3$ represent 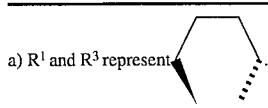

Compound [$I_a$-2]

IR (KRr): 3447, 3422, 3049, 3013, 2680, 1655, 1603, 1558, 1506, 1420, 1387, 1333, 1296, 1257, 1223, 1186, 1148, 1117, 1057, 1024, 953, 887, 851, 818, 785, 746, 706, 683 cm$^{-1}$

IR (KBr): 3431, 3053, 1599, 1493, 1443, 1425, 1385, 1333, 1296, 1223, 1188, 1148, 1128, 1090, 1072, 1045, 1028, 999, 982, 953, 860, 733, 700, 681 cm$^{-1}$

Compound [$I_a$-4]

3447, 3422, 3057, 3041, 2928, 1611, 1558, 1491, 1452, 1420, 1389, 1342, 1310, 1281, 1229, 1213, 1188, 1150, 1126, 1016, 955, 799, 775, 746, 700 cm$^{-1}$

Compound [$I_a$-5]

IR (KBr): 3053, 2922, 2853, 1609, 1555, 1508, 1454, 1423, 1387, 1344, 1327, 1300, 1227, 1188, 1148, 810, 746, 702 cm$^{-1}$

Calcd. for C$_{60}$H$_{45}$N$_2$O$_4$Mn: C, 78.94; H, 4.97; N, 3.07%. Found: C, 79.80; H, 5.32; N, 3.07%

Compound [$I_a$-6]

IR (KBr): 3051, 2920, 1605, 1555, 1508, 1454, 1389, 1344, 1327, 1300, 1221, 1188, 1150, 1126, 810, 770, 704, 687 cm$^{-1}$ Calcd. for C H N O Mn.1.5H O:C, 76.67; H, 5.15; N, 2.98% Found: C, 76.50; H, 5.22; N, 3.06%

Compound [$I_a$-7]

IR (KBr): 3422, 3053, 2932, 2858, 1609, 1583, 1558, 1493, 1423, 1346, 1327, 1223, 1188, 1150, 1124, 1028, 951, 866, 820, 760, 700, 658 cm$^{-1}$

Compound [$I_a$-8]

IR (KBr): 3447, 3051, 2936, 2860, 1611, 1583, 1558, 1508, 1489, 1448, 1423, 1394, 1346, 1329, 1304, 1273, 1225, 1190, 1169, 1150, 1124, 810, 783, 760, 687 cm$^{-1}$

Example 2-1 Epoxidation of indene

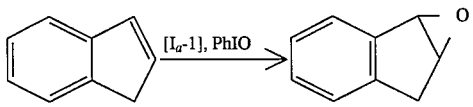

10 μL of indene (86 μmol) was dissolved in 1.1 mL of an acetonitrile solution of pyridine-N-oxide (0.02M, 22 μmol) and added with 2.3 mg of the compound [$I_a$-1] (2.1 μmol). To the solution was added 37.9 mg of iodosylbenzene ( 0.17 mmol ) all at once, followed by stirring at room temperature for twenty four hours. The reaction mixture was concentrated and the residues were purified by silica gel column chromatography (eluent: pentane-pentane-diethyl ether= 10:1) to obtain the intended compound (epoxide yield: 6.0 mg (53%) (asymmetric yield: 92% e.e.).

Example 2-2 Epoxidation of benzopyran

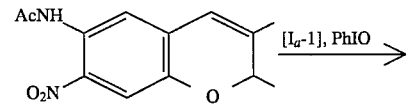

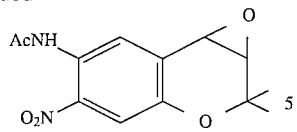

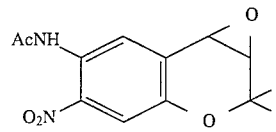

26.2 mg of compound [IV-1] (0.10 mmol) and 2.6 mg of the compound [I$_a$-1] (2.5 μmol) were dissolved in 1.25 mL of an acetonitrile solution of pyridine-N-oxide (0.02 M, 0.025 mmol), followed by cooling to 0° C. To the resulting solution was added 44.0 mg of iodosylbenzene (0.20 mmol) all at once under a nitrogen atmosphere, followed by stirring at 0° C. for twenty four hours. Insoluble matters were filtered out through Celite, the filtrate was concentrated, and the residues were purified by silica gel column chromatography (eluent: hexane-ethyl acetate=8:2–4:6) to obtain the intended compound. (epoxide yield: 20.1 mg (72%)) (asymmetric yield: 98% e.e.) (Daicel Chiralcel OJ, hexane-isopropanol=1:1, flow rate: 0.5 mL/min.)

20.0 mg of compound [IV-1] (76.3 μmol) and 1.7 mg of the compound [I$_a$-1] (1.6 μmol) were dissolved in 760 μL of an acetonitrile solution of N-methylimidazole (0.02M, 7.6 μmol). To the resulting solution was added dropwise 86 μL of 30% hydrogen peroxide (0.76 mmol) over five minutes, followed by stirring at room temperature for twenty four hours. The reaction mixture was concentrated and the residues were purified by silica gel column chromatography (eluent:hexane-ethyl acetate=1:1) to obtain the intended compound. (epoxide yield:7.1 mg (33%)) (asymmetric yield:94% e.e.) (Daicel Chiralcel OJ; hexane-isopropanol=1:1, flow rate=0.5 mL/min.)

Example 2-3 Epoxidation of benzopyran

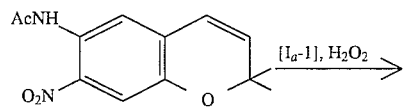

Example 2-4

The same procedure as described in Example 2-3 was repeated to conduct an asymmetric epoxidation on a variety of olefin compounds using-the compound [I$_a$], [I$_b$], [I$_c$] and/or [I$_d$] of the present invention as the catalyst by the aid of iodosylbenzene (PhIO), sodium hypochlorite (NaOCl) or 2-iodosylbenzoic acid (IBA) in acetonitrile. The results are shown in following Table.

| Test No. | Olefin | Compound [I$_a$] | Yield (%) | % e.e. | Abs. confign. |
|---|---|---|---|---|---|
| 1 | naphthalene-based olefin | I$_a$-5 | 41 | 68 | 1S, 2R |
| 2 | naphthalene-based olefin | I$_a$-6 | 52 | 38 | 1R, 2S |
| 3[a)] | naphthalene-based olefin | I$_a$-5 | 67 | 51 | 1S, 2R |
| 4[b)] | naphthalene-based olefin | I$_a$-5 | 71 | 86 | 1S, 2R |
| 5[c)] | naphthalene-based olefin | I$_a$-5 | 77 | 86 | 1S, 2R |
| 6[c)] | naphthalene-based olefin | I$_a$-3 | 96 | 92 | 1S, 2R |

5,599,957

-continued

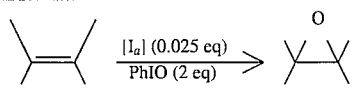

| Test No. | Olefin | Compound [I$_a$] | Yield (%) | % e.e. | Abs. confign. |
|---|---|---|---|---|---|
| 7[c)] | Ph-CH=CH-CH$_3$ | I$_a$-5 | 48[d)] | 89[e)] | 1S, 2R |
| 8[c)] | AcNH-Ar-NO$_2$ (chromene) | I$_a$-5 | 99 | 89 | —[f)] |
| 9[c)] | benzofurazan-chromene | I$_a$-5 | 52 | 91 | —[f)] |
| 10[c)] | benzofurazan-chromene | I$_a$-3 | 69 | 98 | 3R, 5S |

[a)]Methylimidazole was added.
[b)]4-Dimethylaminopyridine N-oxide was added.
[c)]Pyridine N-oxide was added.
[d)]The reaction gave a 3.3:1 mixture of the corresponding cis- and trans- epoxides.
[e)]The number is the % e.e. for the cis-epoxide. The optical purity of the trans-epoxide is 83%.
[f)]Absolute configuration was not determined.

| Test No. | Compound [I$_a$] | Oxidant | Yield (%) | % e.e. |
|---|---|---|---|---|
| 1[a)] | I$_a$-1 | NaOCl | 72 | 95 |
| 2[b)c)] | I$_a$-1 | PhIO | 82 | 94 |
| 3 | I$_a$-1 | PhIO | 52 | 88 |
| 4[a)] | I$_a$-1 | IBA | 60 | 93 |
| 5 | I$_a$-2 | NaOCl | 49 | 82 |
| 6[a)] | I$_a$-2 | NaOCl | 69 | 87 |
| 7[b)] | I$_a$-3 | PhIO | 70 | 85 |
| 8 | I$_a$-3 | NaOCl | 51 | 72 |
| 9[a)] | I$_a$-3 | NaOCl | 67 | 95 |
| 10[a)] | I$_a$-4 | NaOCl | 45 | 55 |
| 11[b)] | I$_a$-7 | PhIO | 55 | 93 |
| 12[a)] | I$_a$-7 | NaOCl | 72 | 95 |
| 13[b)] | I$_a$-8 | PhIO | 60 | 79 |
| 14[a)] | I$_a$-8 | NaOCl | 67 | 93 |
| 15[a)d)] | I$_b$-1[e)] | NaOCl | 80 | 92 |
| 16[a)d)] | I$_a$-3/I$_b$-1 = 1/1[e)] | NaOCl | 83 | 95 |
| 17[a)d)] | I$_a$-3/I$_b$-1 I$_c$+I$_d$[e)] f) = 1/1/1/1 | NaOCl | 87 | 95 |

[a)]4-Phenylpyridine N-oxide was added;
[b)]Pyridine N-oxide was added;

-continued

| Test No. | Compound [I$_a$] | Oxidant | Yield (%) | % e.e. |
|---|---|---|---|---|

[c)]−20° C.
[d)]0° C.
[e)]0.005 equivalent

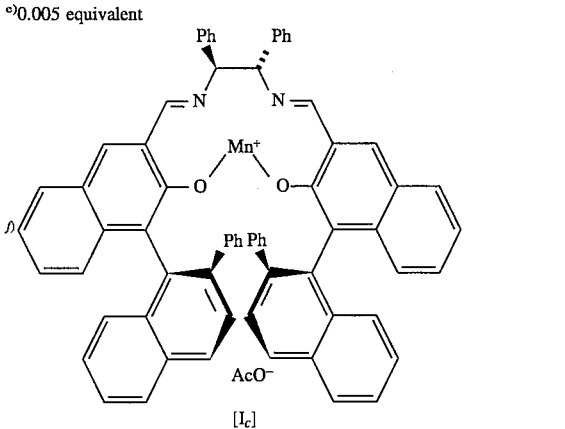

[I$_c$]

-continued

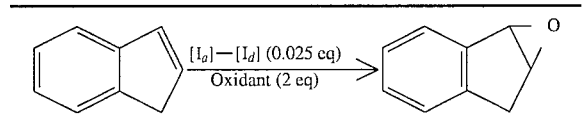

| Test<br>No. | Compound<br>[$I_a$] | Oxidant | Yield (%) | % e.e. |
|---|---|---|---|---|

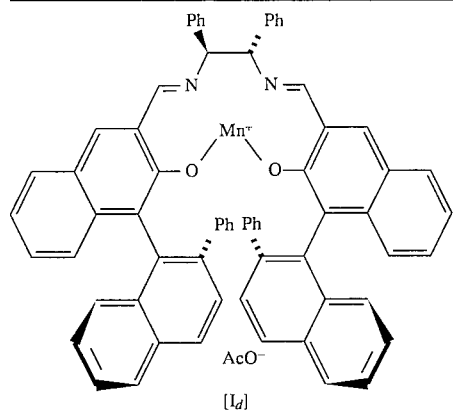

[$I_c$]:[$I_d$] = 1:1

What is claimed is:

1. An optically active material selected from the group consisting of manganese complexes of formula $I_c$, manganese complexes of formula $I_d$, a mixture of manganese complexes of formulae $I_c$ and $I_d$, and mixtures of manganese complexes of formulae $I_c$ and/or $I_d$ with manganese complexes of formulae $I_a$ and/or $I_b$:

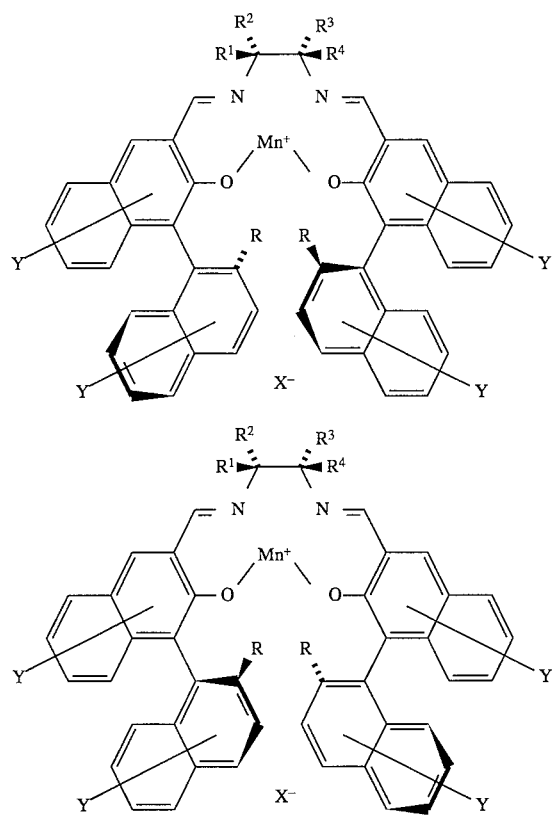

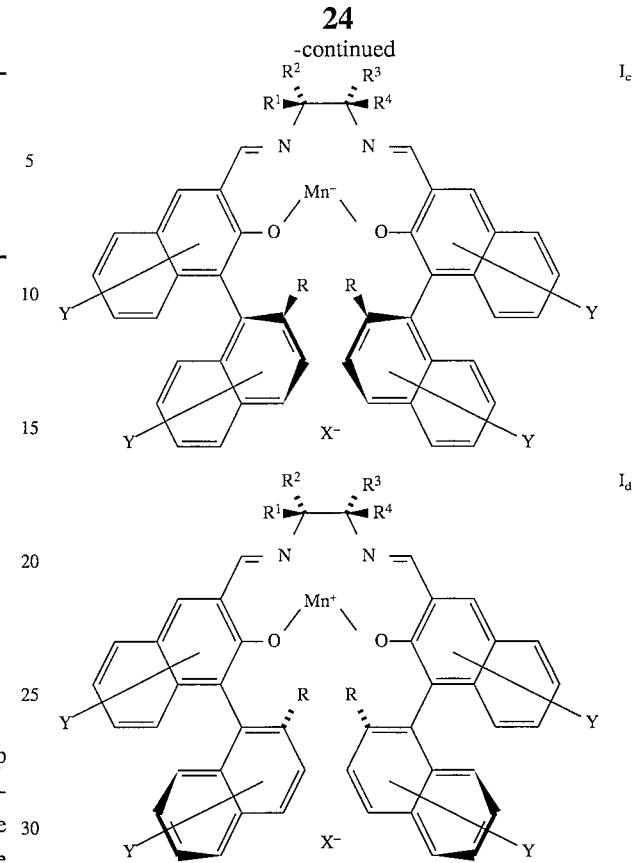

wherein $R^1$, $R^2$, $R^3$ and $R^4$ independently represent hydrogen atom, $C_1$–$C_4$ alkyl group, phenyl group which may be substituted by a halogen atom, $C_1$–$C_4$ alkyl group, $C_1$–$C_4$ alkoxyl group, cyano group or nitro group; and any two of $R^1$, $R^2$, $R^3$ and $R^4$ together form a $C_4$–$C_8$ ring, $X^-$ represents a counter anion which may form a salt, represents hydrogen atom, halogen atom, $C_1$–$C_4$ alkyl group, $C_1$–$C_4$ alkoxyl group, nitro group or cyano group, R represents hydrogen atom, $C_1$–$C_4$ alkyl group, phenyl group which may be substituted by halogen atom, $C_1$–$C_4$ alkyl group or $C_1$–$C_4$ alkoxyl group, or substituted silyl group.

2. An optically active material according to claim 1, wherein said optically active material is manganese complexes of formula $I_c$.

3. An optically active material according to claim 1, wherein said optically active material is manganese complexes of formula $I_d$.

4. An optically active material according to claim 1, wherein said optically active material is a mixture of manganese complexes of formulae $I_c$ and $I_d$.

5. An optically active material according to claim 1, wherein said optically active material is a mixture of manganese complexes of formulae $I_c$ and $I_a$.

6. An optically active material according to claim 1, wherein said optically active material is a mixture of manganese complexes of formulae $I_d$ and $I_a$.

7. An optically active material according to claim 1, wherein said optically active material is a mixture of manganese complexes of formulae $I_c$ and $I_b$.

8. An optically active material according to claim 1, wherein said optically active material is a mixture of manganese complexes of formulae $I_d$ and $I_b$.

9. An optically active material according to claim 1, wherein said optically active material is a mixture of manganese complexes of formulae $I_c$, $I_a$ and $I_b$.

10. An optically active material according to claim 1, wherein said optically active material is a mixture of manganese complexes of formulae $I_d$, $I_a$ and $I_b$.

11. An optically active material according to claim 1, wherein said optically active material is a mixture of manganese complexes of formulae $I_c$, $I_d$ and $I_a$.

12. An optically active material according to claim 1, wherein said optically active material is a mixture of manganese complexes of formulae $I_c$, $I_d$ and $I_b$.

13. An optically active material according to claim 1, wherein said optically active material comprises a mixture of manganese complexes of formulae $I_a$, $I_b$, $I_c$ and $I_d$.

14. An optically active material according to claim 13, wherein said mixture of manganese complexes of formulae $I_a$, $I_b$, $I_c$ and $I_d$ is in a ratio of 1:1:1:1.

15. A process for producing an optically active epoxy compound of formula III:

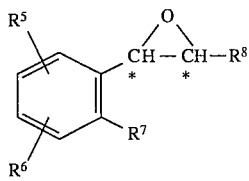

wherein $R^5$ and $R^6$ independently represents a hydrogen atom, cyano group, nitro group, amino group which may be protected by a protecting group, halogen atom, $C_1$–$C_4$ alkyl group, $C_1$–$C_4$ alkoxyl group, halo-$C_1$–$C_4$ alkyl group, carboxyl group, formyl group, $C_1$–$C_4$ alkanoyl group, aroyl group, halo-$C_1$–$C_4$ alkanoyl group, carbamoyl group, $C_1$–$C_4$ alkylsulfinyl group, arylsulfinyl group, $C_1$–$C_4$ alkylsulfonyl group, arylsulfonyl group, sulfonamide group, or mono- or di-$C_1$–$C_4$ alkylsulfonamide group, or if $R^5$ and $R^6$ are at the ortho position, $R^5$ and $R^6$, together with the linking ring, form a group of the formula:

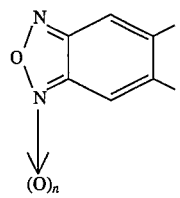

wherein n is 0 or an integer of 1, $R^7$ represents a hydrogen atom, $C_1$–$C_4$ alkyl group or $C_1$–$C_4$ alkoxy group, $R^8$ represents $C_1$–$C_4$ alkyl group or $C_1$–$C_4$ alkoxyl group, $R^7$ and $R^8$ together form the groups of the formulae:

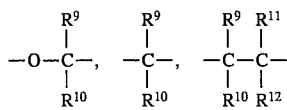

wherein $R^9$, $R^{10}$, $R^{11}$ and $R^{12}$ independently represent a hydrogen atom or $C_1$–$C_4$ alkyl group, and the absolute configuration of the carbon atoms which are marked with asterisks (*) means R or S, comprising:

asymmetrically epoxidizing an olefin compound of the formula II:

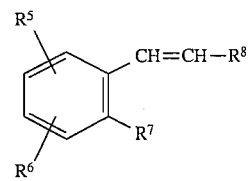

wherein $R^5$, $R^6$, $R^7$ and $R^8$ have the same meanings as defined above, as a starting material, using, as an asymmetric catalyst, an optically active material as claimed in claim 1 to give the compound of the formula III.

16. A process for producing an optically active benzopyran derivative of formula V:

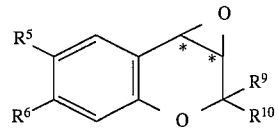

wherein $R^5$ and $R^6$ independently represent a hydrogen atom, cyano group, nitre group, amine group which may be protected by a protecting group, halogen atom, $C_1$–$C_4$ alkyl group, $C_1$–$C_4$ alkoxyl group, halo-$C_1$–$C_4$ alkyl group, carboxyl group, formyl group, $C_1$–$C_4$ alkanoyl group, aroyl group, halo-$C_1$–$C_4$ alkanoyl group, carbamoyl group, $C_1$–$C_4$ alkylsulfinyl group, arylsulfinyl group, $C_1$–$C_4$ alkylsulfonyl group, arylsulfonyl group, sulfonamide group, or mono- or di-$C_1$–$C_4$ alkylsulfonamide group, of if $R^5$ and $R^6$ are at the ortho position, $R^5$ and $R^6$, together with the linking ring, form a group:

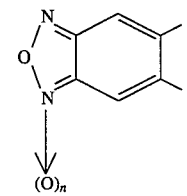

wherein n means 0 or an integer of 1, $R^9$ and $R^{10}$ independently represent hydrogen atom or $C_1$–$C_4$ alkyl group, and the absolute configuration of the carbon atoms which are marked with asterisks (*) means R or S, comprising:

asymmetrically epoxidizing an olefin compound of the formula IV:

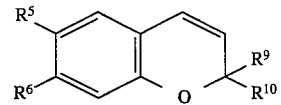

wherein $R^5$, $R^6$, $R^9$ and $R^{10}$ have the same meanings as defined above, using, as an asymmetric catalyst, an optically active material as claimed in claim 1 to give the compound of the formula V.

17. A process for producing an optically active epoxy derivative of formula VII:

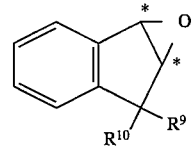

wherein $R^9$ and $R^{10}$ independently represent hydrogen atom or $C_1$–$C_4$ alkyl group, and the absolute configuration of the carbon atoms which are marked with asterisks (*) means R or S, comprising:

asymmetrically epoxidizing a compound of the formula VI:

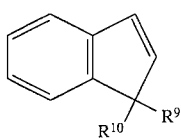
VI wherein $R^9$ and $R^{10}$ have the same meanings as defined above, using, as an asymmetric catalyst, an optically active material as claimed in claim 1 to give the compound of the formula VII.

18. A process for producing an optically active epoxy derivative of formula IX:

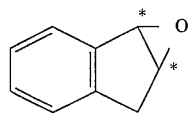
IX wherein the absolute configuration of the carbon atoms which are marked with asterisks (*) means R or S, comprising:

asymmetrically epoxidizing an indene compound of the formula VIII:

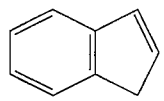
VIII as a starting material, using, as an asymmetric catalyst, an optically active material as claimed in claim 1 to give the compound of the formula IX.

19. A process for producing an optically active epoxy compound of formula III:

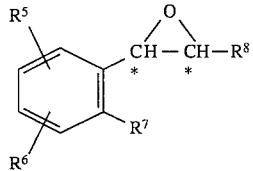
III wherein $R^5$ and $R^6$ independently represents a hydrogen atom, cyano group, nitro group, amino group which may be protected by a protecting group, halogen atom, $C_1$-$C_4$ alkyl group, $C_1$-$C_4$ alkoxyl group, halo-$C_1$-$C_4$ alkyl group, carboxyl group, formyl group, $C_1$-$C_4$ alkanoyl group, aroyl group, halo-$C_1$-$C_4$ alkanoyl group, carbamoyl group, $C_1$-$C_4$ alkylsulfinyl group, arylsulfinyl group, $C_1$-$C_4$ alkylsulfonyl group, arylsulfonyl group, sulfonamide group, or mono- or di-$C_1$-$C_4$ alkylsulfonamide group, or if $R^5$ and $R^6$ are at the ortho position, $R^5$ and $R^6$, together with the linking ring, form a group of the formula:

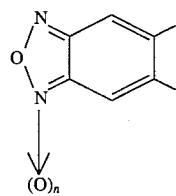

wherein n is 0 or an integer of 1, $R^7$ represents a hydrogen atom, $C_1$-$C_4$ alkyl group or $C_1$-$C_4$ alkoxy group, $R^8$ represents $C_1$-$C_4$ alkyl group or $C_1$-$C_4$ alkoxyl group, $R^7$ and $R^8$ together form the groups of the formulae:

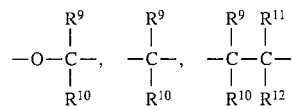

wherein $R^9$, $R^{10}$, $R^{11}$ and $R^{12}$ independently represent a hydrogen atom or $C_1$-$C_4$ alkyl group, and the absolute configuration of the carbon atoms which are marked with asterisks (*) means R or S, comprising:

asymmetrically epoxidizing an olefin compound of the formula II:

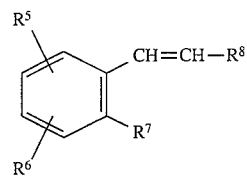
II wherein $R^5$, $R^6$, $R^7$ and $R^8$ have the same meanings as defined above, as a starting material, using, as an asymmetric catalyst, an optically active material as claimed in claim 13 to give the compound of the formula III.

20. A process for producing an optically active benzopyran derivative of formula V:

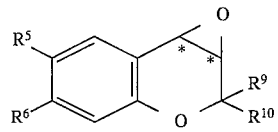
V wherein $R^5$ and $R^6$ independently represent a hydrogen atom, cyano group, nitro group, amino group which may be protected by a protecting group, halogen atom, $C_1$-$C_4$ alkyl group, $C_1$-$C_4$ alkoxyl group, halo-$C_1$-$C_4$ alkyl group, carboxyl group, formyl group, $C_1$-$C_4$ alkanoyl group, aroyl group, halo-$C_1$-$C_4$ alkanoyl group, carbamoyl group, $C_1$-$C_4$ alkylsulfinyl group, arylsulfinyl group, $C_1$-$C_4$ alkylsulfonyl group, arylsulfonyl group, sulfonamide group, or mono- or di-$C_1$-$C_4$ alkylsulfonamide group, of if $R^5$ and $R^6$ are at the ortho position, $R^5$ and $R^6$, together with the linking ring, form a group:

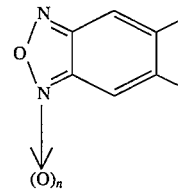

wherein n means 0 or an integer of 1, $R^9$ and $R^{10}$ independently represent hydrogen atom or $C_1$-$C_4$ alkyl group, and the absolute configuration of the carbon atoms which are marked with asterisks (*) means R or S, comprising:

asymmetrically epoxidizing an olefin compound of the formula IV:

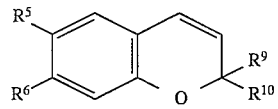
IV wherein $R^5$, $R^6$, $R^9$ and $R^{10}$ have the same meanings as defined above, using, as an asymmetric catalyst, an optically active material as claimed in claim 13 to give the compound of the formula V.

21. A process for producing an optically active epoxy derivative of formula VII:

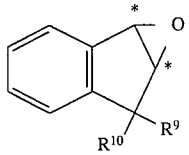

wherein $R^9$ and $R^{10}$ independently represent hydrogen atom or $C_1$–$C_4$ alkyl group, and the absolute configuration of the carbon atoms which are marked with asterisks (*) means R or S, comprising:

asymmetrically epoxidizing a compound of the formula VI:

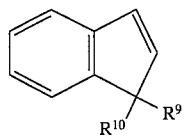

wherein $R^9$ and $R^{10}$ have the same meanings as defined above, using, as an asymmetric catalyst, an optically active material as claimed in claim 13 to give the compound of the formula VII.

22. A process for producing an optically active epoxy derivative of formula IX:

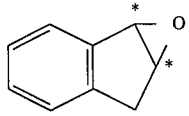

wherein the absolute configuration of the carbon atoms which are marked with asterisks (*) means R or S, comprising:

asymmetrically epoxidizing an indene compound of the formula VIII:

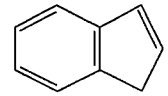

as a starting material, using, as an asymmetric catalyst, an optically active material as claimed in claim 13 to give the compound of the formula IX.

23. A mixture of optically active manganese complexes of formula $I_a$ and $I_b$:

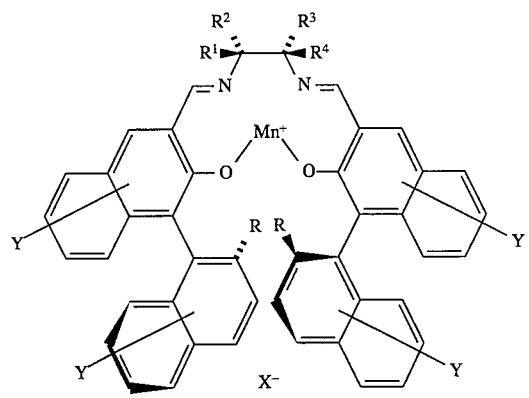

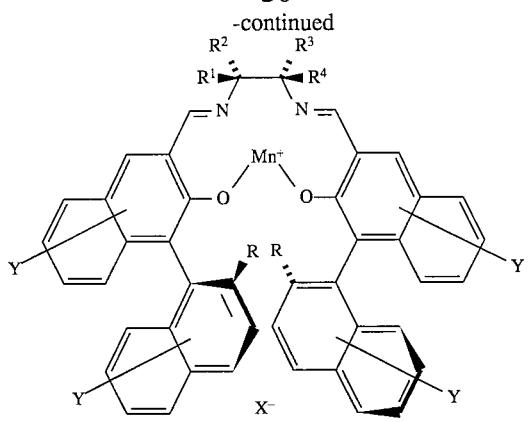

wherein $R^1$, $R^2$, $R^3$ and $R^4$ independently represent hydrogen atom, $C_1$–$C_4$ alkyl group, phenyl group which may be substituted by a halogen atom, $C_1$–$C_4$ alkyl group, $C_1$–$C_4$ alkoxyl group, cyano group or nitro group; and any two of $R^1$, $R^2$, $R^3$ and $R^4$ together form a $C_4$–$C_8$ ring, $X^-$ represents a counter anion which may form a salt, Y represents hydrogen atom, halogen atom, $C_1$–$C_4$ alkyl group, $C_1$–$C_4$ alkoxyl group, nitro group or cyano group, R represents hydrogen atom, $C_1$–$C_4$ alkyl group, phenyl group which may be substituted by halogen atom, $C_1$–$C_4$ alkyl group or $C_1$–$C_4$ alkoxyl group, or substituted silyl group.

24. A process for producing an optically active epoxy compound of formula III:

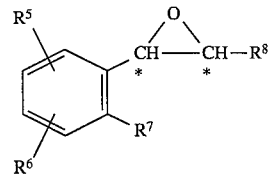

wherein $R^5$ and $R^6$ independently represents a hydrogen atom, cyano group, nitro group, amino group which may be protected by a protecting group, halogen atom, $C_1$–$C_4$ alkyl group, $C_1$–$C_4$ alkoxyl group, halo-$C_1$–$C_4$ alkyl group, carboxyl group, formyl group, $C_1$–$C_4$ alkanoyl group, aroyl group, halo-$C_1$–$C_4$ alkanoyl group, carbamoyl group, $C_1$–$C_4$ alkylsulfinyl group, arylsulfinyl group, $C_1$–$C_4$ alkylsulfonyl group, arylsulfonyl group, sulfonamide group, or mono- or di-$C_1$–$C_4$ alkylsulfonamide group, or if $R^5$ and $R^6$ are at the ortho position, $R^5$ and $R^6$, together with the linking ring, form a group of the formula:

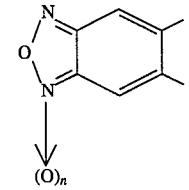

wherein n is 0 or an integer of 1, $R^7$ represents a hydrogen atom, $C_1$–$C_4$ alkyl group or $C_1$–$C_4$ alkoxy group, $R^8$ represents $C_1$–$C_4$ alkyl group or $C_1$–$C_4$ alkoxyl group, $R^7$ and $R^8$ together form the groups of the formulae:

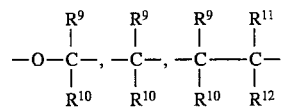

wherein $R^9$, $R^{10}$, $R^{11}$ and $R^{12}$ independently represent a hydrogen atom or $C_1$–$C_4$ alkyl group, and the absolute configuration of the carbon atoms which are marked with asterisks (*) means R or S, comprising:

asymmetrically epoxidizing an olefin compound of the formula II:

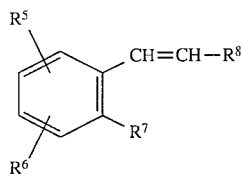

wherein $R^5$, $R^6$, $R^7$ and $R^8$ have the same meanings as defined above, as a starting material, using, as an asymmetric catalyst, an optically active manganese complex mixture comprising a mixture of the optically active manganese complexes of the formula $I_a$ and $I_b$ as claimed in claim 23 to give the compound of the formula III.

25. A process for producing an optically active benzopyran derivative of formula V:

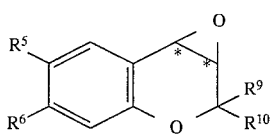

wherein $R^5$ and $R^6$ independently represent a hydrogen atom, cyano group, nitro group, amino group which may be protected by a protecting group, halogen atom, $C_1$–$C_4$ alkyl group, $C_1$–$C_4$ alkoxyl group, halo-$C_1$–$C_4$ alkyl group, carboxyl group, formyl group, $C_1$–$C_4$ alkanoyl group, aroyl group, halo-$C_1$–$C_4$ alkanoyl group, carbamoyl group, $C_1$–$C_4$ alkylsulfinyl group, arylsulfinyl group, $C_1$–$C_4$ alkylsulfonyl group, arylsulfonyl group, sulfonamide group, or mono- or di-$C_1$–$C_4$ alkylsulfonamide group, of if $R^5$ and $R^6$ are at the ortho position, $R^5$ and $R^6$, together with the linking ring, form a group:

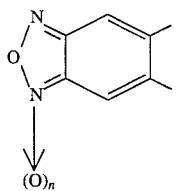

wherein n means 0 or an integer of 1, $R^9$ and $R^{10}$ independently represent hydrogen atom or $C_1$–$C_4$ alkyl group, and the absolute configuration of the carbon atoms which are marked with asterisks (*) means R or S, comprising:

asymmetrically epoxidizing an olefin compound of the formula IV:

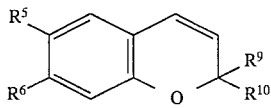

wherein $R^5$, $R^6$, $R^9$ and $R^{10}$ have the same meanings as defined above, using, as an asymmetric catalyst, an optically active manganese complex mixture comprising a mixture of the optically active manganese complexes of the formula $I_a$ and $I_b$ as claimed in claim 23 to give the compound of the formula V.

26. A process for producing an optically active epoxy derivative of formula VII:

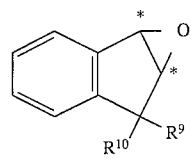

wherein $R^9$ and $R^{10}$ independently represent hydrogen atom or $C_1$–$C_4$ alkyl group, and the absolute configuration of the carbon atoms which are marked with asterisks (*) means R or S, comprising:

asymmetrically epoxidizing a compound of the formula VI:

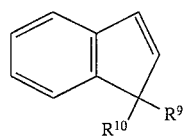

wherein $R^9$ and $R^{10}$ have the same meanings as defined above, using, as an asymmetric catalyst, an optically active manganese complex mixture comprising a mixture of the optically active manganese complexes of the formula $I_a$ and $I_b$ as claimed in claim 23 to give the compound of the formula VII.

27. A process for producing an optically active epoxy derivative of formula IX:

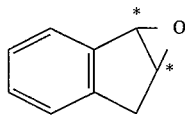

wherein the absolute configuration of the carbon atoms which are marked with asterisks (*) means R or S, comprising:

asymmetrically epoxidizing an indene compound of the formula VIII:

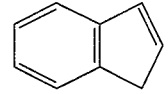

as a starting material, using, as an asymmetric catalyst, an optically active manganese complex mixture comprising a mixture of the optically active manganese complexes of the formula $I_a$ and $I_b$ as claimed in claim 23 to give the compound of the formula IX.

* * * * *